United States Patent
Jeong et al.

(10) Patent No.: US 11,530,429 B2
(45) Date of Patent: Dec. 20, 2022

(54) METHOD FOR PREPARING ISOMALTOOLIGOSACHARIDE COMPOSITION

(71) Applicant: CORN PRODUCTS DEVELOPMENT, INC., Westchester, IL (US)

(72) Inventors: Hea-Seok Jeong, Bridgewater, NJ (US); Jiyoung Song, Bridgewater, NJ (US)

(73) Assignee: CORN PRODUCTS DEVELOPMENT, INC., Westchester, IL (US)

( * ) Notice: Subject to any disclaimer, the term of this patent is extended or adjusted under 35 U.S.C. 154(b) by 0 days.

(21) Appl. No.: 16/959,626

(22) PCT Filed: Dec. 28, 2018

(86) PCT No.: PCT/US2018/067885
§ 371 (c)(1),
(2) Date: Jul. 1, 2020

(87) PCT Pub. No.: WO2019/135994
PCT Pub. Date: Jul. 11, 2019

(65) Prior Publication Data
US 2020/0370082 A1  Nov. 26, 2020

(30) Foreign Application Priority Data

Jan. 2, 2018 (KR) .................. 10-2018-0000274
Oct. 2, 2018 (KR) .................. 10-2018-0117875

(51) Int. Cl.
*C12P 19/24* (2006.01)
*C12P 19/02* (2006.01)

(52) U.S. Cl.
CPC ............. *C12P 19/24* (2013.01); *C12P 19/02* (2013.01)

(58) Field of Classification Search
CPC ........... C12P 19/04; C12P 19/18; C12P 19/12; C12P 19/02; C12P 19/14; C12P 19/24
See application file for complete search history.

(56) References Cited

U.S. PATENT DOCUMENTS 8,637,103 B2 * 1/2014 Kwon ................ C13K 7/00
2008/0121227 A1 * 5/2008 Bhargava ............ C12P 19/14
127/46.1

FOREIGN PATENT DOCUMENTS

| BE | 0 875 585 B1 * | 1/2004 | |
|----|----|----|----|
| BR | 2 805 622 B1 * | 10/2017 | ............. A23L 29/30 |
| EP | 0 875 585 A1 | 11/1998 | |
| EP | 2 805 622 A1 | 11/2014 | |
| WO | 2011017093 A1 | 2/2011 | |

OTHER PUBLICATIONS

Kisselev L., Polypeptide release factors in prokaryotes and eukaryotes: same function, different structure. Structure, 2002, vol. 10: 8-9. (Year: 2002).*

Wishart et al., A single mutation converts a novel phosphotyrosine binding domain into a dual-specificity phosphatase. J. Biol. Chem., 1995, vol. 270(45): 26782-26785. (Year: 1995).*

Witkowski et al., Conversion of b-ketoacyl synthase to a Malonyl Decarboxylase by replacement of the active cysteine with glutamine. Biochemistry, 1999, vol. 38: 11643-11650. (Year: 1999).*

Basu et al., Production of isomaltooligosaccharides (IMO) using simultaneous saccharification and transglucosylation from starch and sustainable sources. Process Biochemistry, 2016, vol. 51: 1464-1471. (Year: 2016).*

Lee et al., Optimized Substrate Concentrations for Production of Long-Chain Isomaltooligosaccharides Using Dextransucrase of Leuconostoc mesenteroides B-512F. J. Microbial. Biotechnol. 2008, vol. 18(6): 1141-1145. (Year: 2008).*

* cited by examiner

*Primary Examiner* — Ganapathirama Raghu
(74) *Attorney, Agent, or Firm* — Rachael Casey

(57) ABSTRACT

This invention provides an isomaltooligosaccharide (IMO) composite and the method to manufacture. According to this invention, isomaltooligosaccharide with a high level of sweetness can be provided without an additional process of adding fructose.

7 Claims, 2 Drawing Sheets

METHOD FOR PREPARING ISOMALTOOLIGOSACCHARIDE COMPOSITION

CROSS-REFERENCE TO RELATED APPLICATIONS

This application is a US National Stage under 35 USC § 371 of International Application No. PCT/US2018/067885, filed Dec. 28, 2018, which claims priority to Korean Patent Application Serial No. 10-2018-000027, filed Jan. 2, 2018, and to Korean Patent Application Serial No. 10-2018-0117875, filed Oct. 2, 2018, both of which are hereby incorporated by reference herein in their entirety.

FIELD OF TECHNOLOGY

This invention is about the method for preparing the isomaltooligosaccharide composite.

PRIOR ART OF INVENTION

Isomaltooligosaccharide (IMO) is oligosaccharide with an exceptional physiological function in humans such as helping beneficial bacteria in the bowel to proliferate and suppressing harmful bacteria and improving constipation. Therefore, it is a functional saccharide substance that leads the oligosaccharide market in Korea and around the world.

However, isomaltooligosaccharide generally does not contain many types of saccharides with high sweetness, about 40-50% of sweetness of sugar. Therefore, a separate component for increasing sweetness such as fructose and glucose is purified, separated, and added during the manufacture process to increase the sweetness of isomaltooligosaccharide. For example, Republic of Korea Patent Publication Number 10-2014-0136244 describes a method for preparing isomaltooligosaccharide, which includes isomaltose, through saccharification by mixing syrup and liquefied solution of purified fructose as the raw saccharide material to produce the quality and degree of sweetness that are differentiated from other existing isomaltooligosaccharide products.

The isomaltooligosaccharide that is produced using the aforementioned method possesses sweetness 1.7-2 times higher than existing isomaltooligosaccharide products. However, it shows an insufficient level of sweetness for replacing sugar at the ratio of 1 to 1. In addition, there are problems such as complex manufacturing and difficult production. Therefore, there is a need to develop a method for preparing isomaltooligosaccharide with simple manufacturing while regaining a high level of sweetness to overcome these problems

DETAILED DESCRIPTION OF INVENTION

Technical Problem

One embodiment is comprised of a method for manufacturing an isomaltooligosaccharide composite including a step to obtain a liquefied solution by combining starch slurry and liquefying enzyme; a step to obtain a liquid saccharide that contains isomaltooligosaccharide by mixing the aforementioned liquefied solution with the primary saccharogenic enzyme and the secondary saccharogenic enzyme; and a step to produce fructose by contacting the aforementioned liquid saccharide with isomerase.

Method of Invention

One embodiment is comprised of a method for manufacturing isomaltooligosaccharide including a step to obtain a liquefied solution by combining starch slurry and liquefying enzyme; a step to obtain a liquid saccharide that contains isomaltooligosaccharide by mixing the aforementioned liquefied solution with the primary saccharogenic enzyme and the secondary saccharogenic enzyme; and a step to produce fructose by contacting the aforementioned liquid saccharide with isomerase.

A detailed example of one embodiment of the aforementioned isomaltooligosaccharide composite may not include isomaltose. Generally, isomaltose is produced when fructose and liquefied solution are reacted using an enzyme. However, the method of one embodiment does not produce isomaltose because fructose solution is not used as the raw material, which results in no production of isomaltose. Subsequently, by not including isomaltose, the content of fructose increases, resulting in the production of an isomaltooligosaccharide composite with a high level of sweetness.

In this detailed description of the invention, the term "oligosaccharide" refers to a carbohydrate that is formed by several saccharides through bonding.

"Isomaltooligosaccharide" is a mixture of short chain carbohydrates and may include glucose oligomers by □-D-(1, 6)-link. Isomaltose, pantose, isomaltotriose, isomaltotetraose, isomaltopentaose, nigerose, kojibiose, or trehalose may be included as a saccharide. The aforementioned oligosaccharide may contain 1 to 9 branched saccharides, and the aforementioned branched saccharides may be comprised of 1 to 8 saccharides. For example, the aforementioned isomaltooligosaccharide may contain 2 branched saccharides such as kojibiose, trehalose, and nigerose.

The aforementioned isomaltooligosaccharides may easily be obtained by a person skilled in the art using enzymes from corn, wheat, barley, bean, rice, potato, sweet potato, barley, or sorghum, and it can be an optional product that is sold commercially.

In this detailed description of the invention, the term "saccharification" refers to a reaction that changes tasteless polysaccharides such as starch to a saccharide with sweetness by hydrolysis. Saccharification may be carried out through an enzymatic reaction or chemical reaction using a saccharogenic enzyme.

The aforementioned starch slurry refers to a suspension of starch powder mixed in an appropriate solvent (for example, water), and the starch ratio in the total weight of the starch slurry can be 20 to 40%, or 25 to 35% (w/w).

A method of one embodiment includes a step to obtain liquefied solution by contacting starch slurry with liquefied enzyme. The aforementioned liquefied enzyme includes an enzyme that liquefies starch and may include alpha-amylase, cyclodextrin glycosyl transferase, or a combination thereof. The aforementioned liquefied enzyme may be 0.04 to 0.05% (w/w) based on the total weight of solid starch slurry. The step for obtaining the liquefied solution by mixing the aforementioned liquefied enzyme with starch slurry may be performed at pH 5.5 to 6.0, temperature 100 to 110° C. for 5 minutes to 180 minutes.

A method of an embodiment includes the step to obtain isomaltooligosaccharides by contacting a primary saccharogenic enzyme and secondary saccharogenic enzyme with the aforementioned liquefied solution. At this time, if the secondary saccharogenic enzyme is contacted with the aforementioned liquefied solution after it comes in contact with the primary saccharogenic enzyme, there is a problem with the content of isomaltooligosaccharides becoming reduced. If the secondary saccharogenic enzyme is contacted with the aforementioned liquefied solution followed by the primary saccharogenic enzyme, there is a problem of an increase in the content of the saccharogenic enzyme that is needed for the production of the saccharified solution. Therefore, the saccharification time of isomaltooligosaccharides can be shortened by contacting the aforementioned primary saccharogenic enzyme and secondary saccharogenic enzyme at the same time. In addition, it is effective for producing saccharified solution with the optimal content of isomaltooligosaccharides. The aforementioned saccharogenic enzyme refers to an enzyme that saccharifies starch. The aforementioned primary saccharogenic enzyme includes enzymes that produce saccharides with a low molecular weight by hydrolyzing starch. After this, the small saccharides with low molecular weights produced here are used as reaction substrates for enzymes such as transglucosidase. The aforementioned primary saccharogenic enzyme may be glucoamylase, alpha-amylase, beta-amylase, isoamylase, pullulanase, or their combinations.

Glucoamylase is an enzyme that makes dextrose by hydrolyzing starch or dextrin, and it can also make dextrose from isomaltooligosaccharide components (□-(1,6) linking) such as branched saccharides in addition to straight chain saccharides through hydrolysis. Therefore, although glucoamylase is not generally used for the production of isomaltooligosaccharides. However, the recipe of making a primary saccharide solution with isomaltooligosaccharides and dextrose only mainly using glucoamylase, which is not generally used for the production of isomaltooligosaccharides, has been developed in one example. Therefore, it can maintain the isomaltooligosaccharides content that can meet the legal specification and degrade all other components to dextrose.

Alpha-amylase is an enzyme that hydrolyzes starch or dextrin randomly and mainly used for the production of IMO since it cannot breakdown the isomaltooligosaccharides (□-(1,6) linkage) component.

Beta-amylase is an enzyme that makes maltose (saccharose) by breaking down starch or dextrin and cannot break down the isomaltooligosaccharide component ((□-(1,6) linkage)).

Pullulanase is an enzyme that breaks down the □-(1,6) link in the saccharide comprised of dextrose with one or two □-(1,6) links in a straight chain such as pullulan (maltotriose or maltotetraose) with about DP 3-5. It breaks down the substances that alpha-amylase or beta-amylase cannot break down and may help transglucosidase make the isomaltooligosaccharide component.

The aforementioned primary saccharogenic enzyme may be 0.02 to 0.08% (w/w) based on the total weight of the solid component of the liquefied solution.

For example, it may be 0.02 to 0.08% (w/w), 0.02 to 0.07% (w/w), 0.02 to 0.06 (w/w), 0.02 to 0.05% (w/w), 0.02 to 0.04% (w/w), 0.03 to 0.08% (w/w), or 0.03 to 0.05%*w.w). At this time, if the content of the primary saccharogenic enzyme is within the aforementioned ranges, there is a problem with reducing the level of sweetness of isomaltooligosaccharides. Also, if it exceeds the aforementioned ranges, there is a problem of the content of isomaltooligosaccharides not meeting the legal requirements.

The aforementioned secondary saccharogenic enzyme includes the enzymes that produces isomaltooligosaccharides. The aforementioned saccharogenic enzymes include transglucosidase, branching enzyme, dextran sucrase, amylose sucrose, and combinations thereof.

Transglucosidase is an enzyme that is used most widely for the production of isomaltooligosaccharides and can produce saccharides that include □-(1,6) links, which is a component of isomaltooligosaccharides. Mainly, the straight chain saccharides with of the degree of polymerization (DP) of 2-4 are used as a substrate, and after breaking down glucose or maltose from straight-chain saccharides, it can produce isomaltooligosaccharide components by linking □-(1,6) links to other sugars with the degree of polymerization of 2-4. Transglucosidase has difficulty reacting directly with substrates (starch, dextrin) with a large molecular weight. Therefore, it is useful for the production of isomaltooligosaccharides if it is reacted with hydrolase such as alpha-amylase, beta-amylase, or pullulanase since good reactive substrates are provided at the same time.

A branching enzyme is an enzyme that makes the □-(1,6) links similar to transglucosidase.

Dextran sucrase and amylose sucrose are enzymes that make isomaltooligosaccharides with a large molecular weight by linking dextrose to a straight chain saccharide after breaking down sugar.

The aforementioned secondary saccharogenic enzyme may be 0.02 to 0.08% (w/w) based on the total weight of the solid component of the liquefied solution. For example, it may be 0.02 to 0.08% (w/w), 0.02 to 0.07% (w/w), 0.02 to 0.06% (w/w), 0.02 to 0.05% (w/w), 0.02 to 0.04% (w/w), 0.03 to 0.08% (w/w), or 0.03 to 0.05% (w/w). At this time, if the content of the secondary saccharogenic enzyme is less than the aforementioned range, there is a problem with the content of isomaltooligosaccharides not meeting the legal requirements in addition to a reduced level of sweetness. The step for obtaining the saccharified solution by contacting the aforementioned primary saccharogenic enzyme and secondary saccharogenic enzyme may be performed for 24 hours to 72 hours at pH 4.7 to 5.5 and temperature 55 to 60° C. At this time, there is a problem of not reaching the optimal content of isomaltooligosaccharides if pH is less than the above range because the optimal pH conditions of the aforementioned primary saccharogenic enzyme and secondary saccharogenic enzyme are different. If the above ranges are exceeded, there is a problem of a reduced level of sweetness of the composite.

A method of one embodiment includes a step to produce fructose by contacting isomerase with the aforementioned saccharified solution. The saccharified solution obtained after the step for obtaining the aforementioned saccharified solution may further include the step for filtering, color removal, ionic exchange, or concentration according to the methods that are well known in the saccharification field.

The aforementioned isomerase may be dextrose isomerase, glucose isomerase, or combinations thereof. The aforementioned isomerase may change dextrose or glucose to fructose.

The isomerization reaction using isomerase may be performed at pH 7.5 to 8.5, or 7.8 to 8.0, temperature 50 to 65° C., or 53 to 60° C., and it may be performed so that the content of dextrose prior to isomerization is 50-90% or 75-90% (w/w) based on the solid component or the content of fructose after isomerization 30 to 45% or 33 to 45% (w/w) based on the solid component. Also, it may be performed when the solid content in the saccharide solution is below 40 brix, below 38 brix, or below 30 brix.

In one embodiment, a step for producing fructose using the aforementioned isomerase is performed after the production of isomaltooligosaccharides. Since the reaction pH (7.5 to 8.5) and reaction temperature of isomerase such as dextrose isomerase are very different than the reaction pH (4.5 to 5.5) and temperature of saccharogenic enzymes, it has been a common knowledge in the saccharide field that isomerase cannot be used with saccharogenic enzymes, which produce isomaltooligosaccharides. However, in one example, the inventors have developed a method for reacting a primary saccharogenic enzyme and secondary saccharogenic enzyme with isomerase by adding isomerase during the manufacturing process of isomaltooligosaccharides. Therefore, the composition of saccharides in the isomaltooligosaccharide composite can be changed freely, and the content of saccharides that are above 3 in the degree of polymerization (DP3+) with low sweetness can be lowered to 5 to 7%. Also, the content of monosaccharides and saccharose with the degree of polymerization 2 or below (DP1, DP2) with high sweetness can be increased to 85 to 97%. Therefore, isomaltooligosaccharides with the sweetness similar to sugar can be produced. In addition, since fructose is produced in the isomaltooligosaccharides manufactured by converting dextrose to fructose, the process for producing and purifying separate saccharides can be omitted in the process of adding to isomaltooligosaccharides. However, it is possible to add fructose as needed. However, the aforementioned isomerase may be in powder or liquid form.

Other embodiments provide the isomaltooligosaccharide composite that includes saccharides with the degree of polymerase 3 or higher of 3 to 10% (w/w), 85 to 97% (w/w) monosaccharide and saccharose.

The aforementioned composite may be an isomaltooligosaccharide composite that includes 75 to 85% (w/w) monosaccharides. Monosaccharides may include glucose, fructose, mannose, galactose, or ribose. The content of the aforementioned fructose may be 30 to 40% (w/w).

According to one embodiment, the isomaltooligosaccharide composite may provide high sweetness due to an increased content from monosaccharide and saccharose with high sweetness. The aforementioned isomaltooligosaccharide composite may be above 88, above 89, above 90, above 91, above 92, above 93, above 94, or above 95 of sweetness.

If the aforementioned composite is a food composite, it can be produced in a common food formulation that is available in the technical field. The aforementioned food composite, for example, may be manufactured in general formulations such as powders, granules, tablets, pills, capsules, suspensions, emulsions, syrups, infusions, solutions, and extracts. It can also be manufactured in any food formats such as meats sausages, breads, chocolates, candies, snacks, confectioneries, pizzas, ramen, other noodles, gums, jellies, dairy products such as ice cream, various soups, beverages, teas, drinks, alcoholic beverages, and multivitamins. To produce the above food items, carriers or additives that are approved for food may be used. Also, optional carriers or additives that have been announced and can be used in the technical field for the manufacture of the desired formulation.

As aforementioned additives, various nutrients, vitamins, electrolytes, flavors, colorants, pectic acid and its salts, alginic acid and its salts, organic acids, protective colloid thickeners, pH adjusters, stabilizers, preservatives, glycerin, alcohols, carbonates used in carbonated drinks may be included. In addition, they may include natural fruit juices, fruit juice drinks, or vegetable drinks. In addition, it may contain pulps to manufacture natural fruit juices, fruit juice drinks, and vegetable drinks. The components of these additives may be used independently or in combination, and the ratio of additives may be 0.001 to 5 weight %, specifically 0.01 to 3 weight %, based on the total weight of the composite.

The aforementioned beverages may use the aforementioned composite as the sweetener and may further contain various flavors and natural carbohydrates that are commonly used for beverages. The aforementioned natural carbohydrates may include common saccharides such as monosaccharide (example: dextrose, fructose, etc.), saccharose (example: maltose, sucrose, etc.), polysaccharide (example: dextrin, cyclodextrin, etc.) and sugar alcohol such as xylitol, sorbitol, and erythritol. Also, natural flavors (example: thaumatin, stevia extract, etc.) and synthetic flavors (example: saccharin, aspartame, etc.) may be used as flavors Effectiveness of Invention According to the method for manufacturing isomaltooligosaccharides of one embodiment, isomaltooligosaccharide with a high level of sweetness may be provided in a cost-effective manner by simplifying the process. Also, it can have a level of sweetness similar to sugar without containing isomaltose and may be used as a sweetener to replace sugar.

DETAILED DESCRIPTION OF INVENTION

Figure 1:
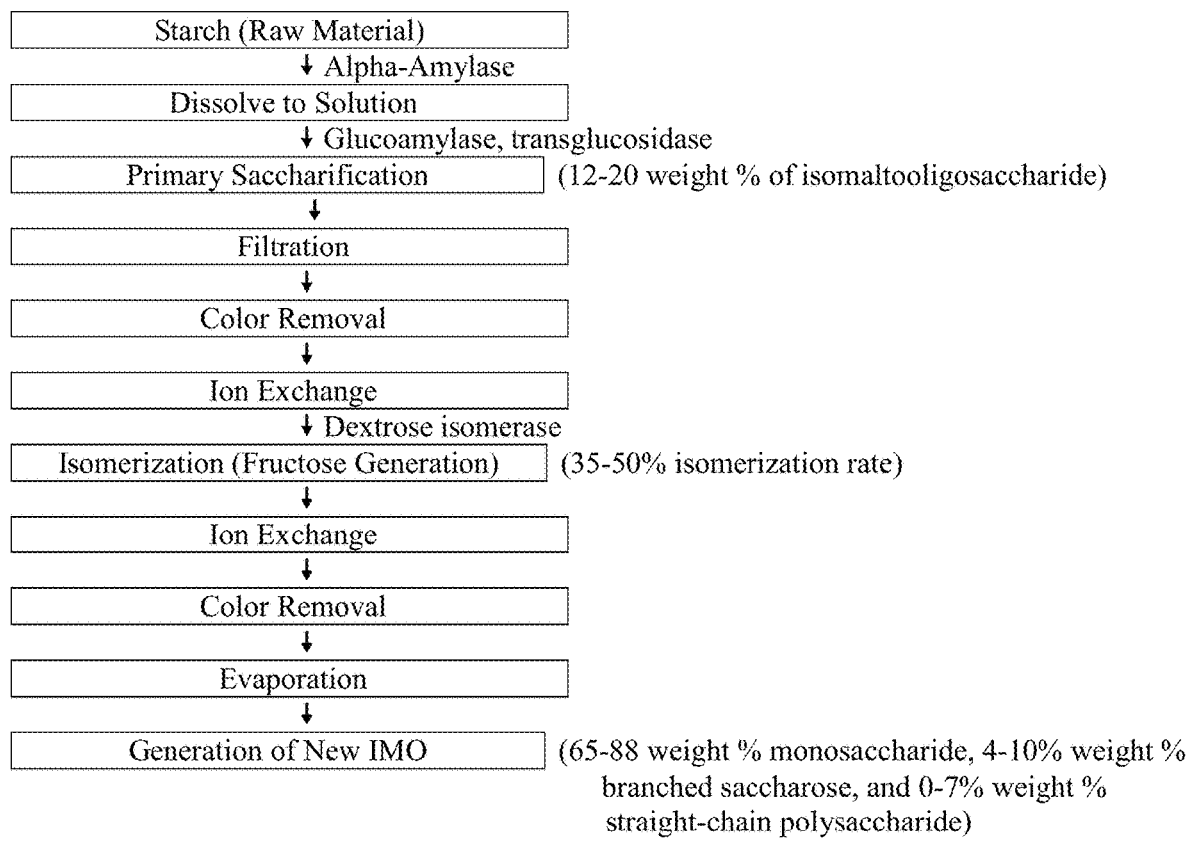
FIG. 1 is a figure that shows the manufacture process of the isomaltooligosaccharide composite briefly in accordance with one embodiment.

Hereafter, recommended examples are provided to help understand this invention. However, these examples provided hereafter are provided to help understand this invention easier and do not limit the scope of this invention.

EXAMPLES

Example 1. Production of Isomaltooligosaccharide Composite

A starch slurry was produced by adding 2,600 g of corn starch and 6,000 g of water in a container.

Alpha-amylase (Liquozyme Supra 2.2X, Novozymes Korea), which is a liquid enzyme) was added to the aforementioned starch slurry at pH 5.5 to 6.0 and 0.04% to 0.05% (w/w) based on the total weight of the solid component of the starch slurry. It was reacted at 100 to 110° C. for 5 to 30 minutes, and a liquefied solution with dextrose equivalent (DE) of 8 to 17 was obtained. Subsequently, a saccharide solution was obtained by mixing the resulting liquefied solution with a saccharogenic enzyme. Specifically, 0.026%-0.06% (w/w) of glucoamylase (Dextrozyme 2.0X, Novozymes) and 0.03%- 0.06% (w/w) of transglucosidase (L "Amano", AMANO) were added at pH 4.8-5.3 based on the total solid weight of the liquefied solution and incubated at 55-60° C. for 24 hours-70 hours.

Isomaltooligosaccharide, which contained dextrose, was obtained in this manner. After this, unreactive substances were filtered, passed and removed color through a carbon column filled with activated carbon granules for 30 minutes to 2 hours at 70 to 75° C. Subsequently, ionic components were removed from the aforementioned solution using a cation exchange resin (PK218, Samyang) and anion exchange resin (WA30, Samyang) at 40 to 50° C. at a flow rate of 50 to 150 L/min. Subsequently, dextrose included in the isomaltooligosaccharide obtained as above was substituted with fructose. Specifically, after obtaining an isomerized solution with a fructose content of 30 to 45% (w/w) based on the solid weight by passing isomaltooligosaccharide through a column filled with isomerase (Gensweet IGI, Dupont) at temperature of 53 to 60° C. and pH 7.5 to 8.0, ionic substances were removed using a cation exchange resin (PK218, Samyang) and anion exchange resin (WA30, Samyang). Coal powder was added to the ionically purified solution at temperature of 70 to 75° C. for 30 minutes to 1 hour to remove color. The solution was passed through 5A and 5C filters, and the isomaltooligosaccharide composite with a high level of sweetness with 75 to 82 Bx was obtained using a concentrator.

Comparative Examples

Comparative Example 1. Production of Isomaltooligosaccharide Composite

The liquefied solution was obtained using the method identical to the aforementioned Example 1. After this, the liquefied solution was obtained by contacting saccharogenic enzyme with the aforementioned liquefied solution. Specifically, glucoamylase (Dextrozyme 2.0X, Novozymes) 0.05%-0.10% (w/w) pH 4.0-4.5 was added based on the total solid weight of the liquefied solution and reacted for 24 hours at 55-60° C.

The non-reactive material of the dextrose solution, which was obtained in this manner, was filtered, and decolorized by passing through a carbon filter filled with granular activated carbon for 30 minutes to 2 hours at 70 to 75° C. Subsequently, ionic components were removed from the aforementioned solution using a cation exchange resin (PK218, Samyang Corp) and anion exchange resin (WA30, Samyang Corp) at 40 to 50° C. and 50 to 150 L/min flow rate. The solution obtained after this was concentrated to 45 to 50 brix and passed through a column filled with isomerase (Gensweet, Dupont) at 54 to 60° C. and pH 7.5 to 8.0 to obtain 40 to 45% isomerized solution based on the solid content of fructose. After this, ionic components were removed from the aforementioned solution using a cation exchange resin (PK218, Samyang Corp) and anion exchange resin (WA30, Samyang Corp) at 40 to 50° C. and 50 to 150 L/min flow rate to obtain a concentrated fructose solution of 55 to 60 brix using a concentrator after decolorization using granular carbon. The aforementioned, concentrated fructose solution was filtered using a column filled with separator resin (Dowex Monosphere 99 ca/320, Dow) at 60 to 62° C. to obtain a highly pure fructose solution with the purity greater than 85% based on the solid weight. After this, ionic components were removed from the aforementioned solution using a cation exchange resin (PK218, Samyang Corp) and anion exchange resin (WA30, Samyang Corp) at 40 to 50° C. and 50 to 150 L/min flow rate and decolorized using granular carbon to obtain a concentrated fructose solution of 70 to 80 brix using a concentrator after decolorization using granular carbon.

Subsequently, a saccharide solution of 35 to 38 brix was produced by mixing with a concentrated fructose solution (55-60 brix), which contains 40 to 45% of the aforementioned fructose, so that the content of fructose is 55 to 57% based on solid weight. The saccharified raw material was produced by mixing the aforementioned liquefied solution 35 to 38 brix) with the aforementioned saccharide solution to about 40% based on the total weight of the aforementioned saccharide solution. After this, 0.03-0.06% of fungal alpha amylase (Clarase L, Dupont), 0.011-0.014% of pullulanase (Optimase L 1000, Dupont), 0.024-0.027% of transglucosidase (Transglucosidase L "Amano", Sein Corporation) were added based on the total weight of the solid content of the saccharified raw material to the saccharified raw material obtained as above. An isomaltooligosaccharide solution was obtained by reacting it at 55 to 60° C. and pH 5.2 to 5.6 for 40 to 48 hours. Unreactive materials of the solution obtained as above were filtered and decolorized by passing through a carbon column filled with active carbon granules at 70 to 75° C. for 30 minutes to 2 hours. Subsequently, ionic components were removed from the aforementioned solution using a cation exchange resin (PK218, Samyang Corp) and anion exchange resin (WA30, Samyang Corp) at 40 to 50° C. and 50 to 150 L/min flow rate. After this, the solution obtained as above was concentrated to 75 to 77 brix to obtain an isomaltooligosaccharide composite.

Comparative Example 2. Production of General Isomaltooligosaccharide Composite

A liquefied solution was obtained using the method identical to Example 1 above. After this, a saccharified solution was obtained by contacting saccharogenic enzyme with the aforementioned liquefied solution. Specifically, 0.03-0.06% of fungal alpha amylase (Clarase L, Dupont), 0.011-0.020% of pullulanase (Optimase L 1000, Dupont), 0.03-0.05% of transglucosidase (Transglucosidase L "Amano", Sein Corporation) was added based on the total weight of the solid content of the liquefied solution and reacted at 55 to 60° C. and pH 5.2 to 5.6 for 40 to 48 hours to obtain an isomaltooligosaccharide solution. Unreactive materials of the solution obtained were filtered and decolorized by passing through a carbon column filled with active carbon granules at 70 to 75° C. for 30 minutes to 2 hours. Subsequently, ionic components were removed from the aforementioned solution using a cation exchange resin (PK218, Samyang Corp) and anion exchange resin (WA30, Samyang Corp) at 40 to 50° C. and a flow rate of 50 to 150 L/min. After this, the solution obtained as above was concentrated to 75 to 77 brix, and an isomaltooligosaccharide composite was obtained.

Test Example

Analysis of the Composition of Saccharide Types in Isomaltooligosaccharide Composite The composition of saccharide types in the isomaltooligosaccharide composites obtained as shown in aforementioned Example 1 and Comparative Examples 1-2 was analyzed. Specifically, the aforementioned composites were analyzed using high-performance liquid chromatography (HPLC), and the results are shown in Table 1 below. At this time, $\varphi$7.8 mm× 300 mm Aminex HPX-42A Carbohydrate column (Manufacturer: Bio-Rad) and $\varphi$4.6 mm×250 mm YMC Polyamine II column were used as the separation columns. The content of each saccharide is the value, which has been converted into percentage based on the total weight of saccharide contained in each saccharide composite or corn syrup, shown in Table 1 below. Also, the content of isomaltooligosaccharide (IMO %) is calculated using the oligosaccharide analysis method of the Food Code.

TABLE 1

| Saccharide Composition (DB %) | Example 1 | Comparative Example 1 | Comparative Example 2 |
|---|---|---|---|
| Fructose | 39.0 | 33.2 | 0.0 |
| Glucose | 41.6 | 35.5 | 24.4 |
| Isomaltose | 0.0 | 6.0 | 0.0 |
| Maltose | 2.4 | 6.2 | 10.80 |
| Isomaltose + kojibiose + nigerose | 11.9 | 8.6 | 11.79 |
| Maltotriose and other higher polysaccharides | 6.9 | 10.6 | 53.01 |
| IMO % | 15.4 | 17.8 | 53.39 |

As a result shown in Table 1, we were able to confirm the content of fructose and glucose, which are monosaccharide components, at a content higher than 78% in Example 1. On the other hand, we were able to confirm the monosaccharide content of about 69% in Comparative Example 1 and monosaccharide content of about 25% in Comparative Example 2. Thus, Example 1 (level of sweetness 95-100) can give stronger sweet taste than Example 1 (level of sweetness 80-85) and Comparative Example 2 (level of sweetness 45-50) due to the different in the content of monosaccharide, which are the components with a high level of sweetness).

Also, unlike the case shown in Comparative Example 1, we were able to confirm that Example 1 did not contain isomaltose. Thus, Example 1 has a different composition of saccharides compared to Comparative Examples 1-2 with a characteristic difference in the quality of sweetness and level of sweetness.

Analysis of Physical Properties of Isomaltooligosaccharide Solution Composite

The viscosity of the isomaltooligosaccharide composites of aforementioned Example 1 and Comparative Examples 1-2 was analyzed, and the results are shown in Table 1 below. Specifically, the aforementioned composite was adjusted to exactly 75.0 brix and analyzed the viscosity using a viscometer.
The viscometer and conditions used for this were Brookfield, spindle no. SCH25, rpm 12, 20° C.

TABLE 2

| | Example 1 | Comparative Example 1 | Comparative Example 2 |
|---|---|---|---|
| Viscosity (cps) 20° C., 75Bx | 1,500 | 1,800 | 2,240 |

As a result shown in Table 2, we were able to confirm that the composite of Example 1 had lower viscosity compared to the composites of Comparative Examples 1-2. Thus, there is a benefit that the composite of Example 1 is easier to use with good flowability compared to Comparative Example 2.

Comparison of Level of Sweetness of Isomaltooligosaccharide Solution Composite

The level of sweetness of the isomaltooligosaccharide composite of aforementioned Example 1 was analyzed. Specifically, 10 professional evaluators in the saccharide field tasted diluted sugar and the composite of Example 1 at 7, 10, 13 brix, and the relative level of sweetness was measured. For an accurate measurement, the test was performed in blind manner, and the evaluators gargled with clean water between tasting to ensure that the order of tasting did not have an effect.

Figure 2:
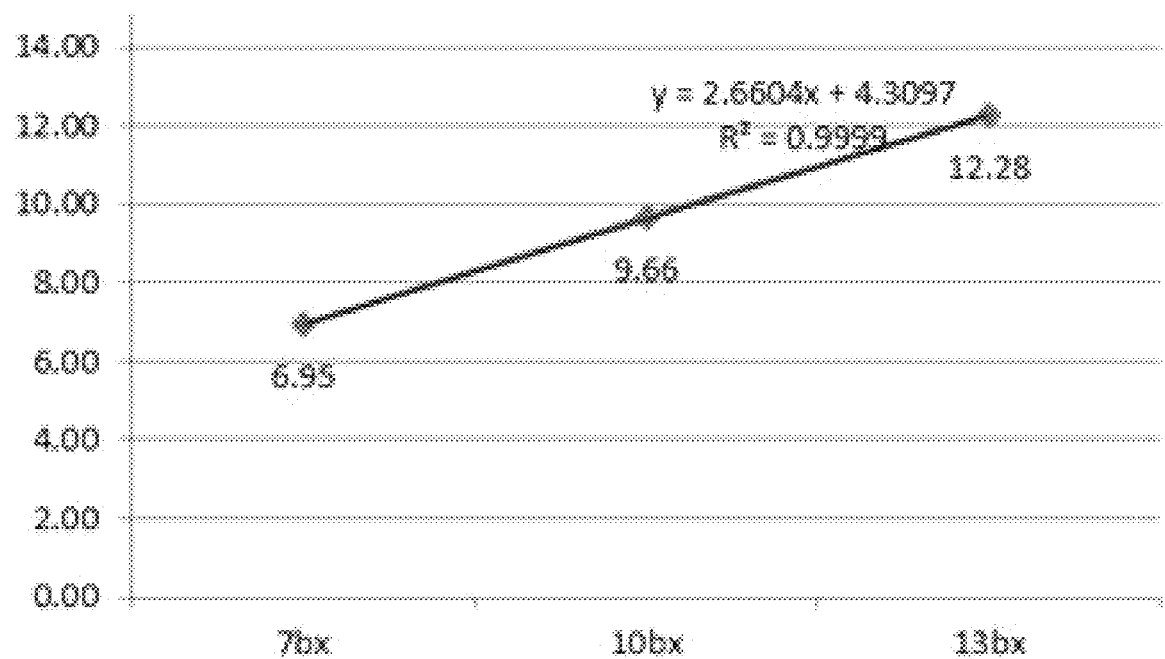
FIG. 2 is a graph that shows the result of the evaluation of the sweetness level of the isomaltooligosaccharide composite in accordance with one embodiment.

As a result shown in FIG. 2, the isomaltooligosaccharide composite of Example 1 was confirmed to show the sugar sweetness level greater than 96%. Thus, the aforementioned composite may be used as a sweetener that can replaced sugar 1 to 1.

Comparison of Sweetness Levels by Content of Saccharide Solution (1) Comparison of Sweetness Levels by Content of Isomaltooligosaccharide
The levels of sweetness (after isomerization) were compared by content of isomaltooligosaccharide of the isomaltooligosaccharide composite of Example 1 above. Specifically, 10 professional evaluators in the saccharide field tasted appropriate amounts of sugar and the composite of Example 1, and the level of sweetness and quality of sweetness were evaluated using a 5-step grading scale (very similar, similar, slightly similar, weak, very week). For accurate measurements, the test was performed in blind manner, and the evaluators gargled with clean water between tasting to ensure that the order of tasting did not have an effect.

TABLE 3

| | Isomaltooligosaccharide Content (w/w based on solid component) | | | |
|---|---|---|---|---|
| Evaluation Items | 10%-35% | 35%-50% | 50%-75% | 75%-100% |
| Comparison with the level of sweetness of sugar (mean) | Similar | Weak | Very weak | Very weak |
| Degree of similarity with the quality of sweetness of sugar (mean) | Similar | Slightly similar | Weak | Weak |

As a result shown in Table 3, when the saccharide solution with the isomaltooligosaccharide content of 10-35% (solid content) was isomerized, the level of sweetness and quality of sweetness were confirmed to be similar to sugar. Therefore, if the aforementioned composite is used as a food composite, it may be used as a sweetener that can replace sugar by including the content of the aforementioned composite at 10-35%.

(2) Comparison of the Level of Sweetness after Isomerization by Glucose Content
The levels of sweetness of the isomaltooligosaccharide composites were compared by glucose content at the saccharification step, prior to the isomerization step. Specifically, the isomaltooligosaccharide composite was manufactured by performing the isomerization step using the method identical to the method described in Example 1 except that the content of glucose was adjusted as shown in Table 4 below in the saccharification step. After this, 10 professional evaluators in the saccharide field tasted 10% (w/w) sugar solution and 10% (w/w) composite of Example 1, and the relative level of sweetness was measured with 100 as the level of sweetness of sugar based on the solid weight. For accurate measurements, the test was performed in a blind manner, and the evaluators gargled with clean water between tasting and with a set rest time to ensure that the order of tasting did not have an effect.

TABLE 4

| Evaluation Items | Glucose Content (w/w based on solid component) | | | |
| --- | --- | --- | --- | --- |
| | 10%-35% | 35%-50% | 50%-75% | 75%-100% |
| Relative Level of Sweetness | Below 60% | 60-75 | 75-105 | 105-115 |

As shown in Table 4, a composite with a better level of sweetness can be manufactured when the content of glucose is above 50-90% in the saccharide solution.

The invention claimed is:

1. A method for producing an isomaltooligosaccharide composite comprising 10 to 35% (w/w) isomaltooligosaccharide and 0% (w/w) isomaltose of the total weight of the composite based on the solid weight of the composite, comprised of:
   a first step to produce a liquefied solution by contacting a starch slurry to a liquifying enzyme;
   a second step to produce an isomaltooligosaccharide saccharified solution by contacting a primary saccharogenic enzyme and a secondary saccharogenic enzyme with the liquefied solution; and followed by
   a third step to produce fructose of 30 to 40% (w/w) based on the total solid weight by contacting isomerase with the isomaltooligosaccharide saccharified solution;
   wherein the primary saccharogenic enzyme is a glucoamylase, alpha-amylase, pullulanase, or a combination thereof,
   wherein the secondary saccharogenic enzyme is a transglucosidase,
   wherein the secondary saccharogenic enzyme is in an amount from 0.03 to 0.08% (w/w) based on the total solid weight of the liquefied solution,
   wherein the primary and secondary saccharogenic enzymes are contacted with the liquified solution for 24 hours to 72 hours at pH 4.7 to 5.5, and at a temperature from 55 to 60° C., and
   wherein the isomaltooligosaccharide composite is comprised of from 85 to 97% (w/w) of monosaccharides or disaccharides.

2. The method according to claim 1, wherein the isomaltooligosaccharide saccharified solution is comprised of 50 to 90% (w/w) of glucose based on the total solid weight of the saccharified solution.

3. The method according to claim 1, wherein the primary saccharogenic enzyme is in an amount from 0.02 to 0.08% (w/w) based on the total solid weight of the liquefied solution.

4. The method according to claim 1, wherein the secondary saccharogenic enzyme is in an amount from 0.03 to 0.05_(w/w) based on the total solid weight of the liquefied solution.

5. An isomaltooligosaccharide composite comprised of saccharides with the degree of polymerization 3 or higher at 3 to 10% (w/w) based on the total solid weight and 85 to 97% (w/w) of monosaccharides or disaccharides, manufactured by the method of claim 1, wherein the isomaltooligosacharide composite comprises 0% isomaltose.

6. The isomaltooligosaccharide composite according to claim 5, wherein the isomaltooligosaccharide composite is comprised of 75 to 85% (w/w) of monosaccharides.

7. The isomaltooligosaccharide composite according to claim 5, wherein the isomaltooligosaccharide composite is comprised of 30 to 40% (w/w) of fructose.

* * * * *